United States Patent [19]

Kung et al.

[11] Patent Number: 4,614,720

[45] Date of Patent: Sep. 30, 1986

[54] HYBRID CELL LINE FOR PRODUCING MONOCLONAL ANTIBODY TO A HUMAN T CELL ANTIGEN, ANTIBODY, AND METHODS

[75] Inventors: Patrick C. Kung, Bridgewater; Gideon Goldstein, Short Hills, both of N.J.

[73] Assignee: Ortho Pharmaceutical Corporation, Raritan, N.J.

[21] Appl. No.: 432,457

[22] Filed: Oct. 4, 1982

Related U.S. Application Data

[62] Division of Ser. No. 110,510, Jan. 8, 1980, Pat. No. 4,364,937.

[51] Int. Cl.$^4$ .................. C12N 5/00; C12P 21/00; C12R 1/91; G01N 33/54
[52] U.S. Cl. .................................... 435/240; 435/68; 435/948; 436/548; 935/104; 935/110
[58] Field of Search ............... 435/240, 241, 41, 68; 436/547, 548; 424/2, 11, 85, 101; 260/112 R, 112 B

[56] References Cited

U.S. PATENT DOCUMENTS 4,364,937 12/1982 Kung et al. .................. 425/85

OTHER PUBLICATIONS

Levy, Ronald, et al., "A Human Thymus-Leukemia Antigen Defined by Hybridoma Monoclonal Antibodies", *Proceedings of the Natl. Academy of Sci.* USA, 76, Dec. '79, pp. 6552–6556.

Emgleman, E. G., et al., "Studies of a Human T Lymphocyte . . . ", Proceedings of the Natl. Academy of Science, USA, 78, Mar. '81, pp. 1791–1795.

*Primary Examiner*—Charles F. Warren
*Assistant Examiner*—John Edward Tarcza
*Attorney, Agent, or Firm*—Geoffrey G. Dellenbaugh

[57] ABSTRACT

Hybrid cell line for production of monocloral antibody to an antigen found on essentially all normal human T cells and on approximately 95% of normal human thymocytes. The hybrid is formed by fusing splenocytes from immunized CAF$_1$ mice with P3X63Ag8U1 myeloma cells. Diagnostic and therapeutic uses of the monoclonal antibody are also disclosed.

1 Claim, 1 Drawing Figure

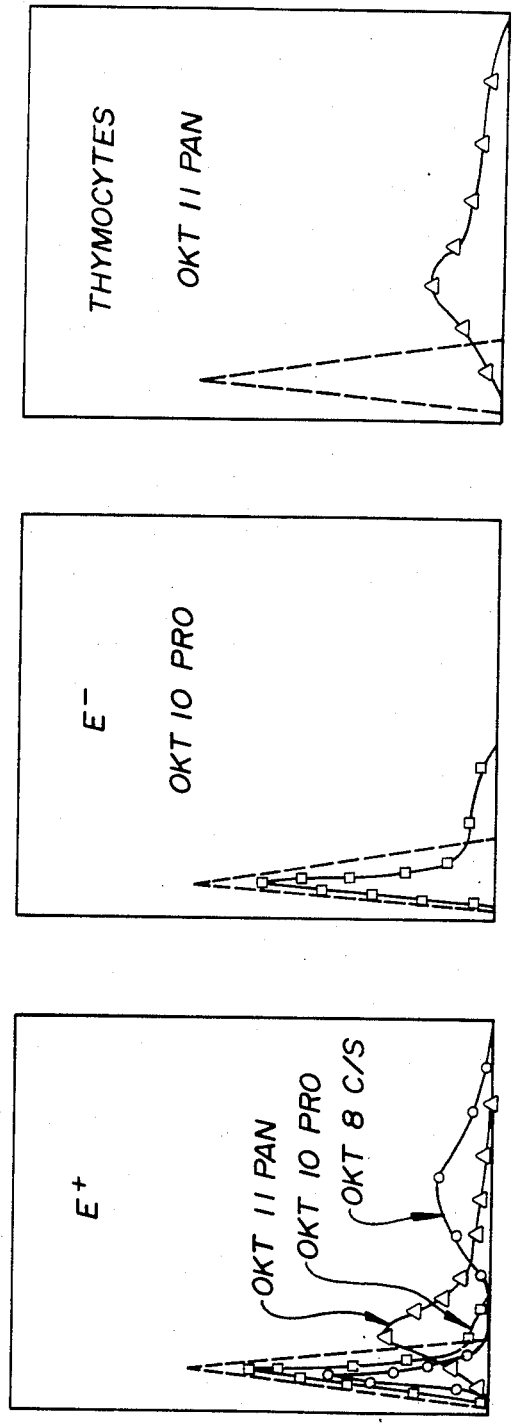

HYBRID CELL LINE FOR PRODUCING MONOCLONAL ANTIBODY TO A HUMAN T CELL ANTIGEN, ANTIBODY, AND METHODS

This is a division of application Ser. No. 110,510 filed Jan. 8, 1980, now U.S. Pat. No. 4,364,937.

FIELD OF THE INVENTION

This invention relates generally to new hybrid cell lines and more specifically to hybrid cell lines for production of monoclonal antibody to an antigen found on essentially all normal human peripheral T cells and on approximately 95% of normal human thymocytes, to the antibody so produced, and to therapeutic and diagnostic methods and compositions employing this antibody.

DESCRIPTION OF THE PRIOR ART

The fusion of mouse myeloma cells to spleen cells from immunized mice by Kohler and Milstein in 1975 [*Nature* 256, 495–497 (1975)] demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. See, for example, *Current Topics in Microbiology and Immunology*, Volume 81-"Lymphocyte Hybridomas", F. Melchers, M. Potter, and N. Warner, Editors, Springer-Verlag, 1978, and references contained therein; C. J. Barnstable, et al., *Cell*, 14, 9–20 (May, 1978); P. Parham and W. F. Bodmer, *Nature* 276, 397–399 (November, 1978); *Handbook of Experimental Immunology*, Third Edition, Volume 2, D. M. Wier, Editor, Blackwell, 1978, Chapter 25; and *Chemical and Engineering News*, Jan. 1, 1979, 15–17. These references simultaneously indicate the rewards and complications of attempting to produce monoclonal antibody from hybridomas. While the general technique is well understood conceptually, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of antigen employed and the selection technique used for isolating the desired hybridoma.

The attempted production of monoclonal antibody to human lymphocyte cell-surface antigens has been reported only in a few instances. See, for example, *Current Topics in Microbiology and Immunology*, ibid, 66–69 and 164–169. The antigens used in these reported experiments were cultured human lymphoblastoid leukemia and human chronic lympnocytic leukemia cell lines. Many hybridomas obtained appeared to produce antibody to various antigens on all human cells. None of the hybridomas produced antibody against a predefined class of human lymphocytes.

More recently, the present applicants and others have authored articles disclosing the preparation and testing of hybridomas making antibody to certain T-cell antigens. See, for example, Reinherz, E. L., et al., *J. Immunol*, 123, 1312–1317 (1979); Reinherz, E. L., et al., *Proc. Natl. Acad. Sci.*, 76, 4061–4065 (1979); and Kung, P. C., et al., *Science*, 206, 347–349 (1979).

It should be understood that there are two principal classes of lymphocytes involved in the immune system of humans and animals. The first of these (the thymus-derived cell or T cell) is differentiated in the thymus from haemopoietic stem cells. While within the thymus, the differentiating cells are termed "thymocytes." The mature T cells emerge from the thymus and circulate between the tissues, lymphatics, and the bloodstream. These T cells form a large proportion of the pool of recirculating small lymphocytes. They have immunological specificity and are directly involved in cell-mediated immune responses (such as graft rejection) as effector cells. Although T cells do not secrete humoral antibodies, they are sometimes required for the secretion of these antibodies by the second class of lymphocytes discussed below. Some types of T cells play a regulating function in other aspects of the immune system. The mechanism of this process of cell cooperation is not yet completely understood.

The second class of lymphocytes (the bone marrow-derived cells or B cells) are those which secrete antibody. They also develop from haemopoietic stem cells, but their differentiation is not determined by the thymus. In birds, they are differentiated in an organ analogous to the thymus, called the Bursa of Fabricius. In mammals, however, no equivalent organ has been discovered, and it is thought that these B cells differentiate within the bone marrow.

It is now recognized that T cells are divided into at least several subtypes, termed "helper", "suppressor", and "killer" T cells, which have the function of (respectively) promoting a reaction, suppressing a reaction, or killing (lysing) foreign cells. These subclasses are well understood for murine systems, but they have only recently been described for human systems. See, for example, R. L. Evans, et al., *Journal of Experimental Medicine*, Volume 145, 221–232, 1977; and L. Chess and S. F. Schlossman-"Functional Analysis of Distinct Human T-Cell Subsets Bearing Unique Differentiation Antigens" in "*Contemporary Topics in Immunobiology*", O. Stutman, Editor, Plenum Press, 1977, Volume 7, 363–379.

The ability to identify or suppress classes or subclasses of T cells is important for diagnosis or treatment of various immunoregulatory disorders or conditions.

For example, certain leukemias and lymphomas have differing prognosis depending on whether they are of B cell or T cell origin. Thus, evaluation of the disease prognosis depends upon distinguishing between these two classes of lymphocytes. See, for example, A. C. Aisenberg and J. C. Long, *The American Journal of Medicine*, 58: 300 (March, 1975); D. Belpomme, et al., in "*Immunological Diagnosis of Leukemias and Lymphomas*", S. Thierfelder, et al., eds, Springer, Heidelberg, 1977, 33–45; and D. Belpomme, et al., *British Journal of Haematology*, 1978, 38, 85.

Certain disease states (e.g., juvenile rheumatoid arthritis, malignancies, and agammaglobulinemia) are associated with an imbalance of T cell subclasses. It has been suggested that autoimmune diseases generally are associated with an excess of "helper" T cells or a deficiency of certain "suppressor" T cells, while agammaglobulinemia is associated with an excess of certain "suppressor" T cells or a deficiency of "helper" T cells. Malignancies generally are associated with an excess of "suppressor" T cells.

In certain leukemias, excess T cells are produced in an arrested stage of development. Diagnosis may thus depend on the ability to detect this imbalance or excess and to determine which developmental stage is in excess. See, for example, J. Kersey, et al., "Surface Markers Define Human Lymphoid Malignancies with Differing Prognoses" in *Haematology and Blood Transfusion*, Volume 20, Springer-Verlag, 1977, 17-24, and references contained therein; and E. L. Reinherz, et al., J. Clin. Invest., 64, 392-397 (1979).

Acquired agammaglobulinemia, a disease state in which no immune globulin is produced, comprises at least two distinct types. In type I the failure to produce immune globulin is due to an excess of suppressor T cells, while in type II it is due to a lack of helper T cells. In both types, there appears to be no defect or lack in the patients' B cells, the lymphocytes which are responsible for the actual secretion of the antibody; however, these B cells are being either suppressed or "not helped", resulting in greatly decreased or absent immune globulin production. The type of acquired agammaglobulinemia may thus be determined by testing for an excess of suppressor T cells or an absence of helper T cells.

On the therapeutic side, there is some suggestion, as yet not definitely proven, that administration of antibodies against the subtype of T cell in excess may have therapeutic benefit in autoimmune disease or malignancies. For example, a helper T cell cancer (certain cutaneous T cell lymphomas and certain T cell acute lymphoblastic leukemias) may be treated by an antibody to a helper T cell antigen. Treatment of autoimmuno disease caused by an excess of helper cells may also be accomplished in the same fashion. Treatment of diseases (e.g., malignancies or type I acquired agammaglobulinemia) due to an excess of suppressor T cells may be treated by administration of an antibody to a suppressor T cell antigen.

Antisera against the entire class of human T cells (so-called antihuman thymocyte globulin or ATG) has been reported useful therapeutically in patients receiving organ transplants. Since the cell-mediated immune response (the mechanism whereby transplants are rejected) depends upon T cells, administration of antibody to T cells prevents or retards this rejection process. See, for example, Cosimi, et al., "Randomized Clinical Trial of ATG in Cadaver Renal Allgraft Recipients: Importance of T Cell Monitoring", *Surgery* 40: 155-163 (1976) and references contained therein; and Wechter, et al., "Manufacture of Antithymocyte Globulin for Clinical Trials", *Transplantation*, 28 (4), 303-307 (1979).

The identification and suppression of human T cell classes and subclasses has previously been accomplished by the use of spontaneous autoantibodies or selective antisera for human T cells obtained by immunizing animals with human T cells, bleeding the animals to obtain serum, and adsorbing the antiserum with (for example) autologous but not allogeneic B cells to remove antibodies with unwanted reactivities. The preparation of these antisera is extremely difficult, particularly in the adsorption and purification steps. Even the adsorbed and purified antisera contain many impurities in addition to the desired antibody, for several reasons. First, the serum contains millions of antibody molecules even before the T cell immunization. Second, the immunization causes production of antibodies against a variety of antigens found on all human T cells injected. There is no selective production of antibody against a single antigen. Third, the titer of specific antibody obtained by such methods is usually quite low, (e.g., inactive at dilutions greater than 1:100) and the ratio of specific to non-specific antibody is less than $1/10^6$.

See, for example, the Chess and Schlossman article referred to above (at pages 365 and following) and the Chemical and Engineering News article referred to above, where the deficiencies of prior art antisera and the advantages of monoclonal antibody are described.

SUMMARY OF INVENTION

There has now been discovered a novel hybridoma (designated OKT11) which is capable of producing novel monoclonal antibody against an antigen found on essentially all normal human peripheral T cells and on approximately 95% of normal human thymocytes, but not on normal human B cells or null cells.

The antibody so produced is monospecific for a single determinant on essentially all normal human peripheral T cells and contains essentially no other anti-human immune globulin, in contrast to prior art antisera (which are inherently contaminated with antibody reactive to numerous human antigens) and to prior art monoclonal antibodies (which are not monospecific for a human T cell and thymocyte antigen). Moreover, this hybridoma can be cultured to produce antibody without the necessity of immunizing and killing animals, followed by the tedious adsorption and purification steps necessary to obtain even the impure antisera of the prior art.

It is accordingly one object of this invention to provide hybridomas which produce antibodies against an antigen found on essentially all of normal human peripheral T cells.

It is a further aspect of the present invention to provide methods for preparing these hybridomas.

A further object of the invention is to provide essentially homogeneous antibody against an antigen found on essentially all normal human peripheral T cells.

A still further object is to provide methods for treatment or diagnosis of disease employing this antibody.

Other objects and advantages of the invention will become apparent from the examination of the present disclosure.

In satisfaction of the foregoing objects and advantages, there is provided by this invention a novel hybridoma producing novel antibody to an antigen found on essentially all normal human peripheral T cells and on approximately 95% of normal human thymocytes (but not on normal human B cells or null cells), the antibody itself, and diagnostic and therapeutic methods employing the antibody. The hybridoma was prepared generally following the method of Milstein and Kohler. Following immunization of mice with leukemic cells from a human with T-cell acute lymphoblastic leukemia (T-ALL), the spleen cells of the immunized mice were fused with cells from a mouse myeloma line and the resultant hybridomas screened for those with supernatants containing antibody which gave selective binding to normal E rosette positive human T cells and/or E⁻ human cells. The desired hybridomas were subsequently cloned and characterized. As a result, a hybridoma was obtained which produces antibody (designated OKT11) against an antigen on essentially all normal human peripheral T cells. Not only does this antibody react with essentially all normal human peripheral T cells, but it also reacts with about 95% of normal human thymocytes but does not react with normal human B cells or null cells.

In view of the difficulties indicated in the prior art and the lack of success reported using malignant cell lines as the antigen, it was surprising that the present method provided the desired hybridoma. It should be emphasized that the unpredictable nature of hybrid cell preparation does not allow one to extrapolate from one antigen or cell system to another. In fact, the present applicants have discovered that the use of a T cell malignant cell line or purified antigens separated from the cell surface as the antigen were generally unsuccessful.

Both the subject hybridoma and the antibody produced thereby are identified herein by the designation "OKT11", the particular material referred to being apparent from the context. The subject hybridoma was deposited on Dec. 13, 1979 at the American Type Culture Collection, 12301 Parklawn Drive, Rockville, Md. 20852, and was given the ATCC accession number CRL 8027.

The preparation and characterization of the hybridoma and the resultant antibody will be better understood by reference to the following description and Examples.

DETAILED DESCRIPTION OF THE INVENTION

The method of preparing the hybridoma generally comprises the following steps:

A. Immunizing mice with leukemic cells from a human with T-ALL. While it has been found that female CAF$_1$ mice are preferred, it is contemplated that other mouse strains could be used. The immunization schedule and thymocyte concentration should be such as to produce useful quantities of suitably primed splenocytes. Three immunizations at fourteen day intervals with $2 \times 10^7$ cells/mouse/injection in 0.2 ml phosphate buffered saline has been found to be effective.

B. Removing the spleens from the immunized mice and making a spleen suspension in an appropriate medium. About one ml of medium per spleen is sufficient. These experimental techniques are well-known.

C. Fusing the suspended spleen cells with mouse myeloma cells from a suitable cell line by the use of a suitable fusion promoter. The preferred ratio is about 5 spleen cells per myeloma cell. A total volume of about 0.5-1.0 ml of fusion medium is appropriate for about $10^8$ splenocytes. Many mouse myeloma cell lines are known and available, generally from members of the academic community or various deposit banks, such as the Salk Institute Cell Distribution Center, La Jolla, CA. The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecular weight from about 1000 to about 4000 (commercially available as PEG 1000, etc.), other fusion promoters known in the art may be employed.

D. Diluting and culturing in separate containers, the mixture of unfused spleen cells, unfused myeloma cells, and fused cells in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1-4) in each separate container (e.g., each well of a microtiter plate). The medium is one (e.g., HAT medium) which will not support the drug resistant (e.g., 8-azaguanine resistant) unfused myeloma cell line. Hence, these myeloma cells perish. Since the unfused spleen cells are non-malignant, they have only a finite number of generations. Thus, after a certain period of time (about one week) these unfused spleen cells fail to reproduce. The fused cells, on the other hand, continue to reproduce because they possess the malignant quality of the myeloma parent and the ability to survive in the selective medium of the spleen cell parent.

E. Evaluating the supernatant in each container (well) containing a hybridoma for the presence of antibody to E rosette positive purified human T cells or thymocytes.

F. Selecting (e.g., by limiting dilution) and cloning hybridomas producing the desired antibody.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are known or are readily determined. This in vitro technique produces essentially monospecific monoclonal antibody, essentially free from other specific antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody is only about 50 $\mu$g/ml.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5-20 mg/ml) in the blood-stream and peritoneal exudate (ascites) of the host mouse. Although these host mice also have normal antibodies in their blood and ascites, the concentration of these normal antibodies is only about 5% of the monoclonal antibody concentration. Moreover, since these normal antibodies are not antihuman in their specificity, the monoclonal antibody obtained from the harvested ascites or from the serum is essentially free of any contaminating antihuman immune globulin. This monoclonal antibody is high titer (active at dilutions of 1:50,000 or higher) and high ratio of specific to non-specific immune globulin (about 1/20). Immune globulin produced incorporating the light myeloma chains are non-specific, "nonsense" peptides which merely dilute the monoclonal antibody without detracting from its specificity.

EXAMPLE I

Production of Monoclonal Antibodies

A. Immunization and Somatic Cell Hybridization

Female $CAF_1$ mice (Jackson Laboratories; 6-8 weeks old) were immunized intraperitoneally with $2 \times 10^7$ human leukemic T-ALL cells in 0.2 ml of phosphate buffered saline at 14-day intervals. Four days after the third immunization, spleens were removed from the mice, and a single cell suspension was made by pressing the tissue through a stainless steel mesh.

Cell fusion was carried out according to the procedure developed by Kohler and Milstein. $1 \times 10^8$ splenocytes were fused in 0.5 ml of a fusion medium comprising 35% polyethylene glycol (PEG 1000) and 5% dimethylsulfoxide in RPMI 1640 medium (Gibco, Grand Island, NY) with $2 \times 10^7$ P3X63Ag8U1 myeloma cells supplied by Dr. M. Scharff, Albert Einstein Colledge of Medicine, Bronx, NY. These myeloma cells secrete $IgG_1$ light chains.

B. Selection and Growth of Hybridoma

After cell fusion, cells were cultured in HAT medium (hypoxanthine, aminopterin, and thymidine) at 37° C. with 5% $CO_2$ in a humid atmosphere. Several weeks later, 40 to 100 μl of supernatant from cultures containing hybridomas were added to a pellet of $10^6$ peripheral lymphocytes separated into E rosette positive ($E^+$) and E rosette negative ($E^-$) populations, which were prepared from blood of healthy human donors as described by Mendes (*J. Immunol.* 111:860, 1973). Detection of mouse hybridoma antibodies binding to these cells was determined by indirect immunofluorescence. Cells incubated with culture supernatants were stained with a fluorescinated goat-anti-mouse IgG (G/M FITC) (Meloy Laboratories, Springfield, VA.; F/p=2.5) and the fluorescent antibody-coated cells were subsequently analyzed on the Cytofluorograf FC200/4800A (Ortho Instruments, Westwood, MA) as described in Example III. Hybridoma cultures containing antibodies reacting specifically with $E^+$ lymphocytes (T cells) and/or thymocytes were selected and cloned twice by limiting dilution methods in the presence of feeder cells. Subsequently, the clones were transferred intraperitoneally by injecting $1 \times 10^7$ cells of a given clone (0.2 ml volume) into $CAF_1$ mice primed with 2,6,10,14-tetramethylpentadecane, sold by Aldrich Chemical Company under the name Pristine. The malignant ascites from these mice were then used to characterize lymphocytes as described below in Example II. The subject hybrid antibody OKT11 was demonstrated by standard techniques to be of $IgG_1$ subclass.

EXAMPLE II

Characterization of OKT11 Reactivity

A. Isolation of Lymphocyte Populations

Human peripheral blood mononuclear cells were isolated from healthy volunteer donors (ages 15-40) by Ficoll-Hypaque density gradient centrifugation (Pharmacia Fine Chemicals, Piscataway, NJ) following the technique of Boyum, *Scand. J. Clin. Lab. Invest.* 21 (Suppl. 97): 77, 1968. Unfractionated mononuclear cells were separated into surface $Ig^+$ (B) and $Ig^-$ (T plus Null) populations by Sephadex G-200 anti-$F(ab')_2$ column chromatography as previously described by Chess, et al., *J. Immunol.* 113:1113 (1974). T cells were recovered by E rosetting the $Ig^-$ population with 5% sheep erythrocytes (microbiological Associates, Bethesda, MD). The rosetted mixture was layered over Ficoll-Hypaque and the recovered $E^+$ pellet treated with 0.155M $NH_4Cl$ (10 ml per $10^8$ cells). The T cell population so obtained was <2% EAC rosette positive and >95% E rosette positive as determined by standard methods. In addition, the non-rosetting $Ig^-$ (Null cell) population was harvested from the Ficoll interface. This latter population was <5% $E^+$ and $\leq 2\%$ $sIg^+$. The surface $Ig^+$ (B) population was obtained from the Sephadex G-200 column following elution with normal human gamma globulin as previously described. This population was >95% surface $Ig^+$ and <5% $E^+$.

B. Isolation of Thymocytes

Normal human thymus gland was obtained from patients aged two months to 14 years undergoing corrective cardiac surgery. Freshly obtained portions of the thymus gland were immediately placed in 5% fetal calf serum in medium 199 (Gibco), finely minced with forceps and scissors, and subsequently made into single cell suspensions by being pressed through wire mesh. The cells were next layered over Ficoll-Hypaque and spun and washed as previously described in section A above. The thymocytes so obtained were >95% viable and $\geq 90\%$ E rosette positive.

EXAMPLE III

Cytofluorographic Analysis and Cell Separation

Cytofluorographic analysis of monoclonal antibodies with all cell populations was performed by indirect immunofluorescence with fluorescein-conjugated goat anti-mouse IgG (G/M FITC) (Meloy Laboratories) utilizing a Cytofluorograf FC200/4800A (Ortho Instruments). In brief, $1 \times 10^6$ cells were treated with 0.15 ml OKT5 at a 1:500 dilution, incubated at 4° C. for 30 minutes, and washed twice. The cells were then reacted with 0.15 ml of a 1:40 dilution G/M FITC at 4° C. for 30 minutes, centrifuged, and washed three times. Cells were then analyzed on the Cytofluorograf, and the intensity of fluorescence per cell was recorded on a pulse height analyzer. A similar pattern of reactivity was seen at a dilution of 1:10,000, but further dilution caused loss of reactivity. Background staining was obtained by substituting a 0.15 ml aliquot of 1:500 ascites from a $CAF_1$ mouse intraperitoneally injected with a non-producing hybrid clone.

BRIEF DESCRIPTION OF THE DRAWINGS

FIG. 1 shows the fluorescence pattern obtained on the Cytofluorograf after reacting normal human thymocytes and $E^+$ and $E^-$ periperhal cells with OKT11 and other monoclonal antibodies at a 1:500 dilution and G/M FITC. Background fluorescence staining was obtained by incubating each population with a 1:500 dilution of ascitic fluid from a mouse injected with a non-producing clone.

The production of the hybridoma and the production and characterization of the resulting monoclonal antibody were conducted as described in the above Examples. Although large quantities of the subject antibody were prepared by injecting the subject hybridoma intraperitoneally into mice and harvesting the malignant ascites, it is clearly contemplated that the hybridoma could be cultured in vitro by techniques well-known in the art and the antibody removed from the supernatant.

Table 1 shows the reactivity of OKT1, OKT3-6, and OKT8-11 with various human lymphoid cell populations. This pattern of reactivity is one test by which the subject antibody OKT11 may be detected and distinguished from other antibodies.

FIG. 1 shows a representative fluorescence pattern obtained on the Cytofluorograf after reacting normal human thymocyte suspensions, and E− and E+ peripheral cells with a 1:500 dilution of OKT11, OKT10, OKT8, and G/M FITC. In contrast to OKT1 and OKT3 T cell antigens (which increase when thymocytes mature to peripheral T cells), that of OKT11 antigen concomitantly decreases. The pattern of reactivity in FIG. 1 is another test by which the subject antibody OKT11 may be detected and distinguished from other antibodies.

Table 2 shows the antigen phenotypes of human T lineage lymphocytes, using OKT11 and other monoclonal antibodies. This phenotype pattern provides a still further way to detect OKT11 antibody and distinguish it from other antibodies.

Table 3 shows the relationship between levels of peripheral T cells and T cell subsets and various disease states. These relationships may be used for diagnostic purposes (e.g., to detect acute infectious mononucleosis) by analyzing the blood sample of an individual suspected of having one of these disease states to determine the levels of T cells and T cell subsets. These relationships may also be used for therapeutic purposes where the cause of the disease state is an elevated level of a T cell subset (e.g., Type I acquired agammaglobulinemia). For therapeutic use, administration of the appropriate monoclonal antibody to a patient with an elevated T cell subset level will decrease or eliminate the excess. The relationships shown in Table 3 are a further way in which OKT11 antibody may be detected and distinguished from other antibodies.

Other monoclonal antibody producing hybridomas prepared by the present applicants (designated OKT1, OKT3, OKT4, and OKT5) are described and claimed in the following U.S. patent applications: Ser. No. 22,132, filed Mar. 20, 1979, now U.S. Pat. No. 4,363,799; Ser. No. 33,639, filed Apr. 26, 1979, now U.S. Pat. No. 4,381,292; Ser. No. 33,699, filed Apr. 26, 1979, now U.S. Pat. No. 4,361,549; and Ser. No. 76,642, filed Sept. 18, 1979, now abandoned; and Ser. No. 82,515, filed Oct. 9, 1979, now U.S. Pat. No. 4,364,932. Still other monoclonal antibody producing hybridomas prepared by the present applicants (designated OKT6, OKT8, OKT9, and OKT10) are described and claimed in U.S. patent applications filed on Dec. 4, 1979, and entitled: Hybrid Cell Line for Producing Monoclonal Antibody to a Human Thymocyte Antigen, Antibody, and Methods; Hybrid Cell Line For Producing Complement-Fixing Monoclonal Antibody to Human Suppressor T Cells, Antibody, and Methods; Hybrid Cell Line For Producing Monoclonal Antibody to Human Early Thymocyte Antigen, Antibody, and Methods; and Hybrid Cell Line For Producing Monoclonal Antibody to a Human Prothymocyte Antigen, Antibody, and Methods. A further hybridoma prepared by the present applicants (designated OKM1) is described and claimed in a U.S. patent application filed on even date herewith and entitled: Hybrid Cell Line for Producing Monoclonal Antibody to a Human Monocyte Antigen, Antibody, and Methods.

These applications are incorporated herein by reference.

According to the present invention there are provided a hybridoma capable of producing antibody against an antigen found on essentially all peripheral T cells and approximately 95% of normal human thymocytes, a method for producing this hybridoma, monoclonal antibody against an antigen found on essentially all normal human peripheral T cells and on approximately 95% of normal human thymocytes, methods for producing the antibody, and methods and compositions for treatment or diagnosis of disease or identification of T cell subclasses employing this antibody.

TABLE 1

| Monoclonal Antibody | Ig Type | Cellular and Tissue Distribution of OKT Antigens | | | | |
|---|---|---|---|---|---|---|
| | | Peripheral Blood (15)* | | Spleen (4) | Bone Marrow (6) | Thymus (15) |
| | | E+ | E− | | | |
| OKT1 | IgG$_1$ | 100** | 0 | 29 ± 9 | <5 | 18 ± 8 |
| OKT3 | IgG$_{2a}$ | 100 | 0 | 31 ± 8 | <5 | 21 ± 8 |
| OKT4 | IgG$_{2b}$ | 64 ± 4 | 0 | 16 ± 3 | <5 | 75 ± 10 |
| OKT5 | IgG$_1$ | 25 ± 4 | 0 | 15 ± 4 | <5 | 77 ± 8 |
| OKT6 | IgG$_1$ | 0 | 0 | 0 | <5 | 68 ± 8 |
| OKT8 | IgG$_{2a}$ | 34 ± 3 | 0 | 17 ± 4 | <5 | 81 ± 7 |
| OKT9 | IgG$_1$ | 0 | 0 | 0 | <5 | 4 ± 3 |
| OKT10 | IgG$_1$ | 5 ± 3 | 13 ± 4 | 10 ± 5 | 16 ± 4 | 96 ± 4 |
| OKT11++ | IgG$_1$ | 100 | 0 | NT+ | NT | 95 ± 3 |

*number of samples examined
**mean ± 1S.D.
+not determined
++five peripheral blood and thymus samples were examined

TABLE 2

| | | Antigen Phenotypes of Human T Lineage Lymphocytes | | | | | | | | |
|---|---|---|---|---|---|---|---|---|---|---|
| | | OKT1 | OKT3 | OKT4 | OKT5 | OKT6 | OKT8 | OKT9 | OKT10 | OKT11 |
| Thymus | Prothymocyte | − | − | − | − | − | − | − | + | − |
| | Early Thymocyte | −(W) | −(W) | + | − | − | − | ± | + | + |
| | Common Thymocyte | −(W) | −(W) | + | + | + | + | ± | + | + |
| | Mature hymocyte | + | + | + | − | − | − | − | + | + |
| Peripheral T Cells | | + | + | − | + | − | + | − | + | + |
| | Inducer (Helper) | + | + | + | − | − | − | − | − | + |
| | Cytotoxic/Suppressor | + | + | − | + | − | + | − | − | + |

W = very weak immunofluorescence

TABLE 3

| PERIPHERAL MONONUCLEAR CELL LEVELS IN DISEASE STATES | | | | | | | |
|---|---|---|---|---|---|---|---|
| | Mononuclear Cell Levels | | | | | | |
| Disease State | OKT3+ | OKT4+ | OKT5 | OKT8 | OKT6 | OKT11 | OKM1 |
| Primary Biliary Cirrhosis (2) | N | + | − | − | − | ++ | − |

TABLE 3-continued
PERIPHERAL MONONUCLEAR CELL LEVELS IN DISEASE STATES

| Disease State | Mononuclear Cell Levels | | | | | | |
|---|---|---|---|---|---|---|---|
| | OKT3+ | OKT4+ | OKT5 | OKT8 | OKT6 | OKT11 | OKM1 |
| Multiple Sclerosis (advanced disease) (8) | − | N | − | − | − | − | + |
| Myasthenia Gravis (early untreated) (3) | O | O | O | O | O | − | + |
| Acute Graft vs Host (3) | O to − | − | O | + | + | + | − |
| Acquired Agammaglobulinemia | | | | | | | |
| Type I | | | + | | | | |
| Type II | | O | | | | | |
| Hyper IgE (4) | − | N | O to − | O to − | − | + | N |
| Acute Infectious Mononucleosis (4)* | + | O to − − | ++ | ++ | O | ++ | − |
| Hodgkins Disease | | | | | | | |
| Stages I & II | N | N | N | N | O | O | N |
| Stages III & IV | − − | N | N | N | O | O | ++ |
| Psoriasis (3/5) | N | +to ++ | N | N | O | N | N |

N = within normal limits
O = absent
+ = above normal
++ = greatly above normal
− = below normal
− − = greatly below normal
*these levels return to normal about one week prior to the disappearance of clinical symptoms
The numbers in parentheses indicate the number of patients evaluated.

Although only a single hybridoma producing a single monoclonal antibody against a human thymocyte antigen is described, it is contemplated that the present invention encompasses all monoclonal antibodies exhibiting the characteristics described herein. It was determined that the subject antibody OKT11 belongs to the subclass $IgG_1$, which is one of four subclasses of murine IgG. These subclasses of immune globulin G differ from one another in the so-called "fixed" regions, although an antibody to a specific antigen will have a so-called "variable" region which is functionally identical regardless of which subclass of immune globulin G it belongs to. That is, a monoclonal antibody exhibiting the characteristic described herein may be of subclass $IgG_1$, $IgG_{2a}$, $IgG_{2b}$, or $IgG_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse antibodies. Although the subject antibody is specifically $IgG_1$, it is contemplated that antibodies having the patterns of reactivity illustrated herein are included within the subject invention regardless of the immune globulin class or subclass to which they belong.

Further included within the subject invention are methods for preparing the monoclonal antibodies described above employing the hybridoma technique illustrated herein. Although only one example of a hybridoma is given herein, it is contemplated that one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having the reactivity characteristics described above are included within the subject invention, as are methods for making this antibody employing the hybridoma.

Further aspects of the invention are methods of treatment or diagnosis of disease employing the monoclonal antibody OKT11 or any other monoclonal antibody exhibiting the pattern of reactivity provided herein. The subject antibody may be employed to diagnose disease states as shown in Table 3. These techniques may be employed using OKT11 antibody alone or in combination with other antibodies (e.g., OKT3-OKT10). Patterns of reactivity with a panel of antibodies to T cells and T cell subsets will allow more precise detection of certain disease states than is possible using prior diagnostic methods.

Treatment of undesired states manifesting themselves as an excess of OKT11+ cells may be accomplished by administration of a therapeutically effective amount of OKT11 antibody to an individual in need of such treatment. By selective reaction with OKT11+ antigen, the effective amount of OKT11 antibody will reduce the excess of OKT11+ cells, thus ameliorating the effects of the excess. Diagnostic and therapeutic compositions comprising effective amounts of OKT11 antibody in admixture with diagnostically or pharmaceutically acceptable carriers, respectively, are also included within the present invention.

Since peripheral T cells are responsible for graft rejection, one example of a therapeutic use of OKT11 antibody is the administration to a graft recipient of an amount of OKT11 antibody effective to reduce or eliminate the graft rejection. In this way OKT11 antibody could be substituted for the anti-thymocyte globulin discussed above with a significant increase in specificity.

What is claimed is:

1. A hybridoma having the identifying characteristics of ATCC CRL 8027.

* * * * *